United States Patent
De Sapio

(10) Patent No.: US 10,409,928 B1
(45) Date of Patent: Sep. 10, 2019

(54) GOAL ORIENTED SENSORIMOTOR CONTROLLER FOR CONTROLLING MUSCULOSKELETAL SIMULATIONS WITH NEURAL EXCITATION COMMANDS

(71) Applicant: HRL Laboratories, LLC, Malibu, CA (US)

(72) Inventor: Vincent De Sapio, Westlake Village, CA (US)

(73) Assignee: HRL Laboratories, LLC, Malibu, CA (US)

( * ) Notice: Subject to any disclaimer, the term of this patent is extended or adjusted under 35 U.S.C. 154(b) by 1056 days.

(21) Appl. No.: 14/539,898

(22) Filed: Nov. 12, 2014

Related U.S. Application Data

(60) Provisional application No. 61/903,526, filed on Nov. 13, 2013.

(51) Int. Cl.
*A61F 4/00* (2006.01)
*G06F 17/50* (2006.01)
*G16H 50/50* (2018.01)

(52) U.S. Cl.
CPC ......... *G06F 17/5009* (2013.01); *G16H 50/50* (2018.01)

(58) Field of Classification Search
None
See application file for complete search history.

(56) References Cited

U.S. PATENT DOCUMENTS

2007/0172797 A1*  7/2007  Hada ..................... G09B 23/32
434/1
2007/0256494 A1* 11/2007  Nakamura ............. A61B 5/224
73/379.01
2013/0310979 A1* 11/2013  Herr ..................... B62D 57/032
700/258

OTHER PUBLICATIONS

Carlos Rengifo et al. "Optimal control of a neuromusculoskeletal model: a second order sliding mode solution", 2008 IEEE, p. 55-60.*
Fady Alnajjar et al. "A bio-inspired neuromuscular model to simulate the neuro-sensorimotor basis for postural-reflex-response in Humans", The Fourth IEEE RAS/EMBS International Conference on Biomedical Robotics and Biomechatronics Roma, Italy. Jun. 24-27, 2012, p. 980-985.*
Vincent De Sapio et al "Task-level approaches for the control of constrained multibody systems" (Year: 2006).*

(Continued)

*Primary Examiner* — Timothy A Mudrick
*Assistant Examiner* — Abdou K Seye
(74) *Attorney, Agent, or Firm* — Tope-McKay & Associates

(57) ABSTRACT

Described is a goal-oriented sensorimotor controller for generating musculoskeletal simulations with neural excitation commands. The controller receives a task-level motion command for motion of a musculoskeletal system, the musculoskeletal system having musculoskeletal dynamics that include steady state tendon forces. The controller then generates, based on the task-level motion command, a set of muscle activations associated with the steady state tendon forces. A set of excitation commands are then generated that minimizes required muscle activations amongst the set of muscle activations to generate motion consistent with the task-level motion command, thereby performing a musculoskeletal simulation.

15 Claims, 11 Drawing Sheets

(56) References Cited

OTHER PUBLICATIONS

Crowninshield, R.D. and Brand, R.A. (1981) 'A physiologically based criterion of muscle force prediction in locomotion', Journal of Biomechanics, vol. 14, No. 11, pp. 793-801.

Davy, D.T. and Audu, M.L. (1987) 'A dynamic optimization technique for predicting muscle forces in the swing phase of gait', Journal of Biomechanics, vol. 20, No. 2, pp. 187-201.

De Sapio, V. (2011) 'Task-level control of motion and constraint forces in holonomically constrained robotic systems', in Proceedings of the 18th World Congress of the International Federation of Automatic Control, pp. 14622-14629.

De Sapio, V. and Park, J. (2010) 'Multitask constrained motion control using a mass-weighted orthogonal decomposition', Journal of Applied Mechanics, vol. 77, No. 4, pp. 041004-1 through 041004-10.

De Sapio, V., Khatib, O., and Delp, S. (2006) 'Task-level approaches for the control of constrained multibody systems', Multibody System Dynamics, vol. 16, No. 1, pp. 73-102.

Khatib, O. (1995) 'Inertial properties in robotic manipulation: an object level framework', International Journal of Robotics Research, vol. 14, No. 1, pp. 19-36.

Khatib, O., Sentis, L., Park, J., and Warren, J. (2004) 'Whole-body dynamic behavior and control of human-like robots', International Journal of Humanoid Robotics, vol. 1, No. 1, pp. 29-43.

Sentis, L., Park, J. and Khatib, O. (2010) 'Compliant control of multicontact and center-of-mass behaviors in humanoid robots', IEEE Transactions on Robotics, vol. 26, No. 3, pp. 483-501.

Andersen, R. A., Hwang, E. J., & Mulliken, G. H., (2010), Cognitive neural prosthetics, Annual review of psychology, 61, 169.

Bouganis, A., & Shanahan, M., (Jul. 2010), Training a spiking neural network to control a 4-DoF robotic arm based on spike timing-dependent plasticity, in Neural Networks (IJCNN), The 2010 International Joint Conference on (pp. 1-8), IEEE.

Buneo, C. A., Jarvis, M. R., Batista, A. P., & Andersen, R. A., (2002), Direct visuomotor transformations for reaching, Nature, 416(6881), 632-636.

Davoodi, R., & Loeb, G. E., (Feb. 2011). MSMS software for VR simulations of neural prostheses and patient training and rehabilitation, in MMVR (pp. 156-162).

Davoodi, R., Urata, C., Hauschild, M., Khachani, M., & Loeb, G. E., (2007), Model-based development of neural prostheses for movement, Biomedocal Engineering, IEEE Transactions on, 54(11), 1909-1918.

De Sapio, V., Khatib, O., & Delp, S., (2008), Least action principles and their application to constrained and task-level problems in robotics and biomechanics, Multibody System Dynamics, 19(3), 303-322.

Dethier, J., Nuyujukian, P., Eliasmith, C., Stewart, T. C., Elasaad, S. A., Shenoy, K. V., & Boahen, K. A., (2011), A brain-machine interface operating with a real-time spiking neural network control algorithm. In Advances in Neural Information Processing Systems (pp. 2213-2221).

Hauschild, M., Davoodi, R., & Loeb, G. E., (2007), A virtual reality environment for designing and fitting neural prosthetic limbs, Neural Systems and Rehabilitation Engineering, IEEE Transactions on; 15(1), 9-15.

Hochberg, L. R., Bacher, D., Jarosiewicz, B., Masse, N. Y., Simeral, J. D., Vogel, J., . . . & Donoghue, J. P., (2012), Reach and grasp by people with tetraplegia using a neurally controlled robotic arm, Nature, 485(7398), 372-375.

Khatib, O., (1995), Inertial properties in robotic manipulation: An object-level framework, The International Journal of Robotics Research, 14(1), 19-36.

Lebedev, M. A., Tate, A. J., Hanson, T. L., Li, Z., O'Doherty, J. E., Winans, J. A., . . . & Nicolelis, M. A., (2011), Future developments in brain-machine interface research, Clinics, 66, 25-32.

Naidu, D. S., Chen, C. H., Perez, A., & Schoen, M. P., (Aug. 2008), Control strategies for smart prosthetic hand technology: An overview, in Engineering in Medicine and Biology Society, EMBS 2008. 30th Annual International Conference of the IEEE (pp. 4314-4317), IEEE.

Sabes, P. N., (2000), The planning and control of reaching movements. Current opinion in neurobiology, 10(6), 740-746.

Srinivasa, N., & Cho, Y., (2014), Self-organizing spiking neural model for learning fault-tolerant spatio-motor transformations, Neural Networks and Learning Systems, IEEE Transactions on. 23(10), 1526-1538.

Velliste, M., Perel, S., Spalding, M. C., Whitford, A. S., & Schwartz, A. B., (2008), Cortical control of a prosthetic arm for self-feeding, Nature, 453(7198), 1098-1101.

De Sapio, V. (2011), Task-level control of motion and constraint forces in holonomically constrained robotic systems, in Proceedings of the 18th World Congress of the International Federation of Automatic Control.

De Sapio, V. and Park, J. (2010), Multitask constrained motion control using a mass-weighted orthogonal decomposition, Journal of Applied Mechanics, vol. 77, No. 4, p. 041004.

De Sapio, V., Khatib, O, and Delp, S. (2005), Simulating the task-level control of human motion: a methodology and framework for implementation, The Visual Computer, vol. 21, No. 5, pp. 289-302.

Thelen, D.G. and Anderson, F.C. (2006), Using computed muscle control to generate forward dynamic simutations of human walking from experimental data, Journal of Biomechanics,vol. 39, No. 6, p. 1107.

Thelen, D.G., Anderson, F.C. and Delp, S.L. (2003), Generating dynamic simulations of movement using computed muscle control, Journal of Biomechanics, vol. 36, No. 3, pp. 321-328.

Bhattacharyya, R., Musallam, S., & Andersen, R. A. (2009), Parietal reach region encodes reach depth using retinal disparity and vergence angle signals. Journal of neurophysiology, 102(2), 805-816.

V. De Sapio. (2014) An approach for goal-oriented neuromuscular control of digital humans. International Journal of Human Factors Modelling and Simulation, 4(2):121-144.

V. De Sapio, J. Warren, O. Khatib, and S. Delp. (2005). Simulating the task-level control of human motion: A methodology and framework for implementation. The Visual Computer, 21(5):289-302.

F. E. Zajac, (1989). Muscle and tendon: properties, models, scaling, and application to biomechanics and motor control. Critical reviews in biomedical engineering, 17(4), 359-411.

Anderson, F. C., & Pandy, M. G. (2001). Dynamic Optimization of Human Walking. Journal Biomechanical Engineering , 123 (5), 381-390.

Anderson, F. C., & Pandy, M. G. (2001). Static and dynamic optimization solutions for gait are practically equivalent. Journal of Biomechanics , 34, 153-161.

Bogacz, R., Brown, E., Moehlis, J., Holmes, P., & Cohen, J. D. (2006). The physics of optimal decision making: a formal analysis of models of performance in two-alternative forced-choice tasks. Psychologicai review , 113 (4), 700-765.

Crowninshield, R. D., & Brand, R. A. (1981). A physiologically based criterion of muscle force prediction in locomotion. Journal of Biomechanics , 14, 793-801.

Davy, D. T., & Audu, M. L. (1987). A dynamic optimization technique for predicting muscle forces in the swing phase of gait. Journal of Biomechanics , 20 (2), 187-201.

Hopfield, J. J., & Tank, D. W. (1985). "Neural" computation of decisions in optimization problems. Biological cybernetics , 52 (3), 141-152.

Kaplan, M. L., & Heegaard, J. H. (2001). Predictive algorithms for neuromuscular control of human locomotion. Journal of Biomechanics , 34, 1077-1083.

Siciliano, B., & Khatib, O. (Eds.). (2008). Chapter 6, Section 6.6, pp. 143-146, Springer Handbook of Robotics, Springer.

Mansouri, M., & Reinbolt, J. A. (2012). Journal of Biomechanics A platform for dynamic simulation and control of movement based on OpenSim and MATLAB , 45 (8), 1517-1521.

Neptune, R. R. (1999) Optimization algorithm performance in determining optimal controls in human movement analyses, Journal of Biomechanical Engineering , 121, 249-252.

(56) References Cited

OTHER PUBLICATIONS

Selen, L. P., Shadlen, M. N., & Wolpert, D. M. (2012). Deliberation in the motor system: Reflex gains track evolving evidence leading to a decision. The Journal of Neuroscience , 32 (7), 2276-2286.
Thelen, D. G., & Anderson, F. C. (2006). Using computed muscle control to generate forward dynamic simulations of human walking from experimental data. Journal of Biomechanics , 39, 1107-1115.
Thelen, D. G., Anderson, F. C., & Delp, S. L. (2003), Generating dynamic simulations of movement using computed muscle control. Journal of Biomechanics , 36 (3), 321-328.
S. Goldfarb, R. Bhattacharyya, and V. De Sapio, "Coupled Models of Cognition and Action: Behavioral Phenotypes in the Collective," Collective Intelligence 2014, Poster Session, Massachusetts Institute of Technology.
Lewis, F.L., Abdallah, C.T. and Dawson, D.M. (1993) in "Control of Robot Manipulators", Macmillan Publishing Company, New York, Chapter 4, pp. 169-260.

\* cited by examiner

GOAL ORIENTED SENSORIMOTOR CONTROLLER FOR CONTROLLING MUSCULOSKELETAL SIMULATIONS WITH NEURAL EXCITATION COMMANDS

CROSS-REFERENCE TO RELATED APPLICATIONS

This is a non-provisional patent application of U.S. Provisional Application No. 61/903,526, filed Nov. 13, 2013, entitled, "A goal-oriented sensorimotor controller for controlling musculoskeletal simulations with neural excitation commands."

BACKGROUND OF TIE INVENTION

(1) Field of Invention

The present invention relates to a control system and, more particularly, to a goal-oriented sensorimotor controller for controlling musculoskeletal simulations with neural excitation commands.

(2) Description of Related Art

Biomechanical simulation has become increasingly important to the clinical biomedical community in areas like orthopedic surgical planning, rehabilitation, sports medicine, and biomedical device design. Additionally, there is an emerging need for high-fidelity biomechanical simulations in industrial domains like human factors engineering. Traditionally, human factors analysis has relied on ergonomic data tables derived from exhaustive human subject studies and ad hoc rules-of-thumb, rather than predictive biomechanical science. Computer simulation has been introduced into the human factors community but this has involved the use of simple kinematic manikins operating in a virtual environment in concert with ergonomics data tables and equations from controlled experiments. In these simulations, motion is kinematically key framed (broken up into a set of intermediate poses) and is not representative of human motion. These simulations also provide limited information about human physiological and performance characteristics. Even in case of high-fidelity, biomechanical simulations for clinical application de novo synthesis of human motor control is difficult and often involves demanding open-loop optimization studies.

Dynamic optimization has been used to determine optimal neuromuscular excitations to generate specific motions in musculoskeletal models. See for example, the work of Davy, D. T. and Audu, M. L. (1987), in 'A dynamic optimization technique for predicting muscle forces in the swing phase of gait', Journal of Biomechanics, Vol. 20, No. 2, pp. 187-201, Kaplan, M. L. and Heegaard, J. H. (2001) in 'Predictive algorithms for neuromuscular control of human locomotion', Journal of Biomechanics, Vol. 34, No. 8, pp. 1077-1083, Neptune, R. R. (1999) in 'Optimization algorithm performance in determining optimal controls in human movement analyses', Journal of Biomechanical Engineering, Vol. 121, No. 2, pp. 249-252, and Anderson, F. C. and Pandy, M. G. (2001 a) in 'Dynamic optimization of human walking', Journal of Biomechanical Engineering, Vol. 123, No. 5, pp. 381-390, all of which is hereby incorporated by reference as though fully set forth herein.

In dynamic optimization, the objective function is typically a global measure of biomechanical cost. While providing a globally optimal control history over a time window, dynamic optimization offers a number of disadvantages. Foremost, it is an open-loop technique that finds an optimal solution given a forward dynamical model of the biomechanical system. Further, dynamic optimization suffers from sensitivity to model parameters and lack of robustness to disturbances. Additionally, such a technique is computationally expensive. Alternatively, static optimization using an inverse dynamical model of the biomechanical system (see Crowninshield, R. D. and Brand, R. A. (1981) in 'A physiologically based criterion of muscle force prediction in locomotion', Journal of Biomechanics, Vol. 14, No. 11, pp. 793-801) is computationally less demanding and has been shown to produce results for human gait that are practically equivalent to dynamic optimization (see, for example, Anderson, F. C. and Pandy, M. G. (2001b) in 'Static and dynamic optimization solutions for gait are practically equivalent'. Journal of Biomechanics, Vol. 34, No. 2, pp. 153-161), both of which are hereby incorporated by reference as though fully set forth herein.

A closed-loop control technique employing static optimization has been proposed and demonstrated by Thelen, D. G. and Anderson, F. C. (2006) in 'Using computed muscle control to generate forward dynamic simulations of human walking from experimental data', Journal of Biomechanics, Vol. 39, No. 6, p. 1107, and Thelen et al. (2003) in 'Generating dynamic simulations of movement using computed muscle control', Journal of Biomechanics, Vol. 36, No. 3, pp. 321-328, both of which are hereby incorporated by reference as though fully set forth herein. Referred to as computed muscle control, this technique is analogous to computed torque control for robotic systems. Computed torque control was described by Lewis, F. L., Abdallah, C. T. and Dawson, D. M. (1993) in "Control of Robot Manipulators", Macmillan Publishing Company, New York, which is hereby incorporated by reference as though fully set forth herein. In computed torque control, a desired joint space control trajectory is specified and the necessary control input to the musculoskeletal system is computed. Due to the added complexity of muscle actuated biomechanical systems relative to a torque actuated robotic systems, the computed muscle control technique employs added complexity over computed torque control. This includes a static optimization step to compute optimal steady state muscle activation (consistent with the desired motion) and an excitation controller to account for muscle activation dynamics (i.e., compute excitations that track the optimal steady state muscle activations). While the computed muscle approach has received a large number of citations and has been implemented within a widely used software application (such as OpenSim), it has the disadvantage of being formulated in joint space. OpenSim is a freely available, user extensible software system that lets users develop models of musculoskeletal structures and create dynamic simulations of movement. OpenSim is developed by The National Center for Simulation in Rehabilitation Research (NCSRR), which is a National Center for Medical Rehabilitation Research supported by NIH research infrastructure grant R24 HD065690.

As noted above, the computed muscle approach has the disadvantage of being formulated in joint space. Consequently, motion command inputs require a complete description of the biomechanical system configuration. Additionally, the computed muscle approach does not have a unified way of dealing with reaction forces (internal and external), although ad hoc incorporation of such forces has been presented for specific examples.

Another scheme for motion control of human-like systems has emerged out of the robotics research community. The whole body control framework for humanoid robot control is based on the operational space approach as described by Khatib, O., Sentis, L., Park, J., and Warren, J. (2004) in 'Whole-body dynamic behavior and control of human-like robots', International Journal of Humanoid Robotics, Vol. 1, No. 1, pp. 29-43, Sentis, L., Park, J. and Khatib, O. (2010) in 'Compliant control of multicontact and center-of-mass behaviors in humanoid robots', IEEE Transactions on Robotics, Vol. 26, No. 3, pp. 483-501, and Khatib, O. (1995) in 'Inertial properties in robotic manipulation: an object level framework', International Journal of Robotics Research, Vol. 14, No. 1, pp. 19-36, all of which are incorporated by reference as though fully set forth herein. This offers a task-level abstraction for goal-oriented motion control. However, the whole body control framework has the limitation of not addressing muscle-based actuation and is thus not suitable for the control of simulated musculoskeletal systems.

Thus, a continuing need exists for a sensorimotor controller that incorporates both high-level goal-oriented control abstractions with low-level neuromuscular control primitives for simulated musculoskeletal systems.

SUMMARY OF INVENTION

Described is a goal-oriented sensorimotor controller for generating musculoskeletal simulations with excitation commands. The controller includes one or more processors and a memory. The memory includes executable instructions encoded thereon, such that upon execution of the instructions, the one or more processors perform operations several operations, such as receiving a task-level motion command for motion of a musculoskeletal system, the musculoskeletal system having musculoskeletal dynamics that include steady state tendon forces. The controller also generates, based on the task-level motion command, a set of required muscle activations that minimizes a magnitude squared of the set of required muscle activations amongst a set of all possible muscle activations, where the set of the required muscle activations are associated with the steady state tendon forces. A set of excitation commands is generated that is consistent with the minimization of the magnitude of required muscle activations amongst the set of all possible muscle activations to generate motion consistent with the task-level motion command, thereby performing a musculoskeletal simulation.

In another aspect, the musculoskeletal dynamics of the musculoskeletal system is augmented with holonomically constrained system dynamics and Lagrange multipliers.

Additionally, the set of excitation commands is generated using a linear proportional controller.

In yet another aspect, the holonomically constrained system dynamics are represented in task space as:

$$\bar{J}^{T^T}\tau = \Lambda(q)\ddot{x} + \mu(q,\dot{q}) + p(q) - \bar{J}^T\Phi^T(\alpha+\rho),$$

where $\bar{J}^T$ is a dynamically consistent inverse of the constraint task Jacobian, $^T$ is a constraint null space projection matrix, $\tau$ is a vector of applied joint torques, where $\Lambda(q)$, $\mu(q,\dot{q})$, and $p(q)$, are the task space mass matrix, centrifugal and Coriolis force vector, and gravity force vector, respectively, and where the centrifugal and Coriolis forces, and gravity forces projected at the constraints are $\alpha$ and $\rho$ respectively, and where x is a description of task coordinates that are to be controlled.

In another aspect, the holonomically constrained system dynamics are represented in task space as:

$$\tau = {}^T\bar{J}^T(\Lambda_c\ddot{x} + \mu_c + p_c) + \Phi^T(\alpha+\rho) + U_c^T\tau_N - \Phi^T\lambda,$$

$\tau$ is a vector of applied joint torques, $^T$ is a constraint null space projection matrix, where $\bar{J}^T$ is a dynamically consistent inverse of the constraint task Jacobian, where $\Lambda(q)$, $\mu(q,\dot{q})$, and $p(q)$, are the task space mass matrix, centrifugal and Coriolis force vector, and gravity force vector, respectively, and where the centrifugal and Coriolis forces, and gravity forces projected at the constraints are $\alpha$ and $\rho$ respectively, where $U_c^T$ is the combined null space projection matrix, with respect to both task and constraints, and where $\tau_N$ is the control vector for the null space, and where $\lambda$ is a Lagrange multipliers, and where x is a description of task coordinates that are to be controlled.

Finally and as noted above, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
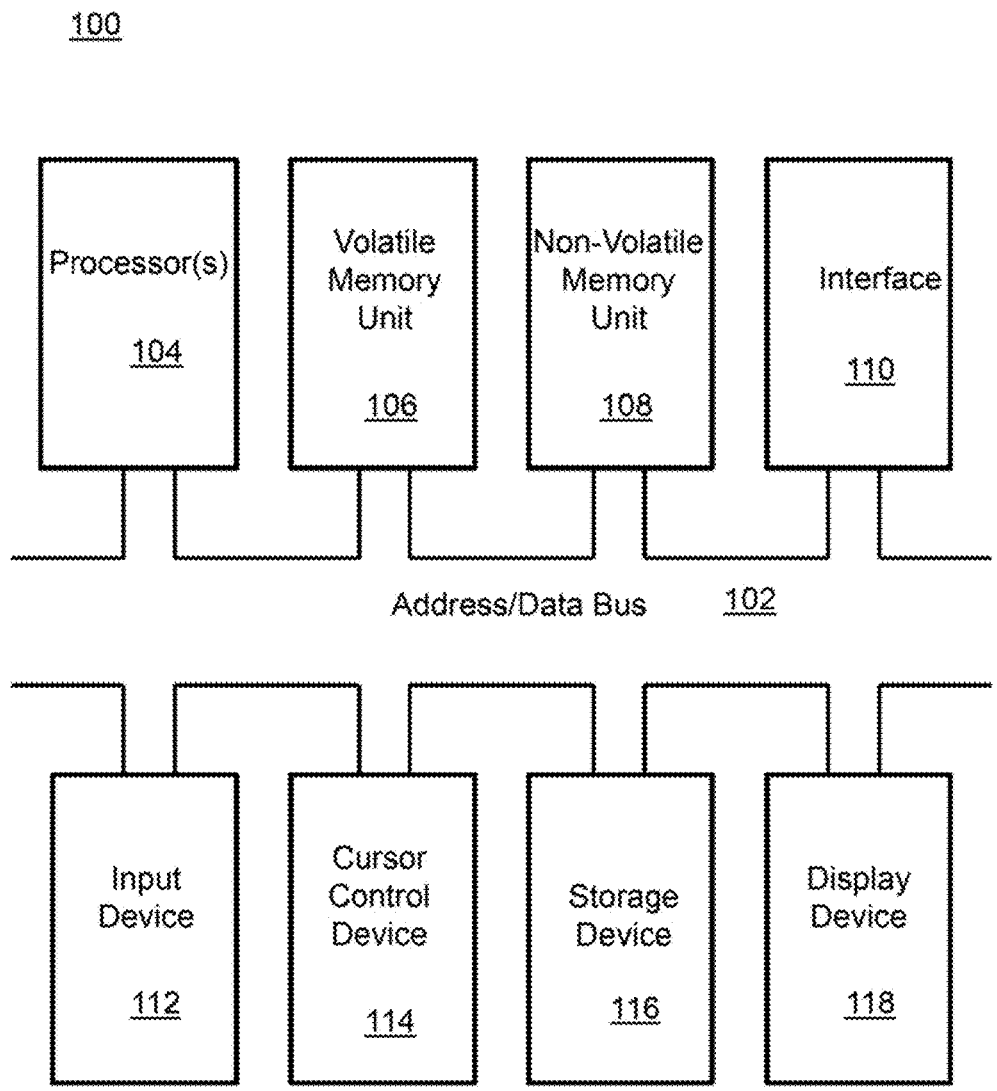
FIG. 1 is a block diagram depicting the components of a system according to the principles of the present invention.

The present invention relates to a control system and, more particularly, to a goal-oriented sensorimotor controller for controlling musculoskeletal simulations with neural excitation commands. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a description of the various principal aspects of the present invention is provided. Subsequently, an introduction provides the reader with a general understanding of the present invention. Finally, specific details of the present invention are provided to give an understanding of the specific aspects.

(1) Principal Aspects

The present invention has three "principal" aspects. The first is goal-oriented sensorimotor controller for controlling musculoskeletal simulations with neural excitation commands. The controller includes all of the necessary hardware for sensing and generation commands, including, in one aspect, a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, or a field programmable gate array.

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
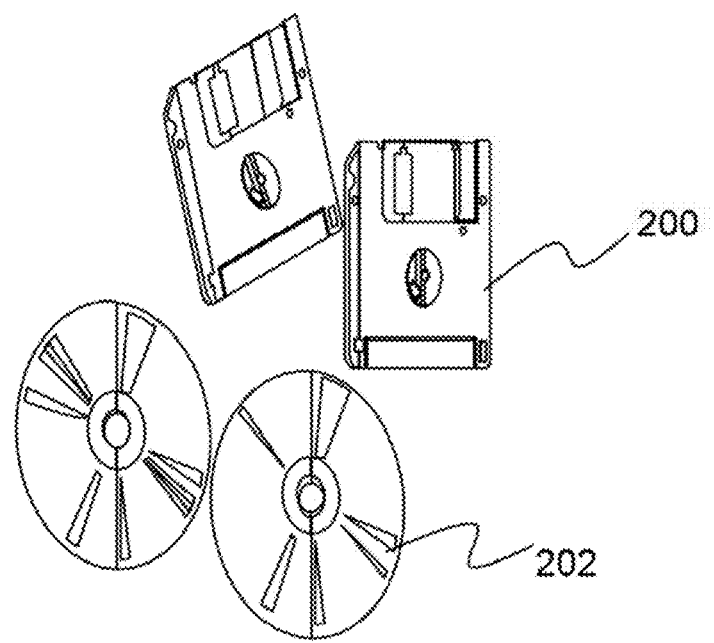
FIG. 2 is an illustration of a computer program product embodying an aspect of the present invention.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(2) Introduction

The system described herein provides goal oriented sensorimotor controller that provides control in task-space. This maintains greater consistency with how commands from the higher motor centers of the brain are encoded. It also allows for much easier specification of desired motion by the user (clinician, human factors engineer, etc.) since the entire motion does not need to be specified, but rather, only goal relevant components of the motion are specified (e.g. "move the right hand to location 1 and the left hand to location 2").

This controller provides a solution for generating biologically plausible neuromuscular control signals to drive musculoskeletal bio-mechanic simulations using goal-oriented command inputs. Constraints associated with biomechanical system are also addressed. These constraints can involve any conditions internal to the biomechanical system, or between the biomechanical system and the external environment that can be expressed as algebraic relations (holonomic constraints). The controller described herein is the only known approach that accommodates a goal-oriented command structure into a closed-loop neuromuscular control architecture. In so doing, it emulates the transmission of goal-oriented commands, generated in the higher-level motor planning and control centers of the brain, to the lower-level motor execution centers of the central nervous. By simulating biological sensorimotor control inputs to the musculoskeletal system, given high-level motor intent from the brain, the system provides a unique approach to goal-oriented control of musculoskeletal biomechanical simulations in a closed loop without the need for offline open-loop generation of neural excitations. The underlying capability for this goal-oriented sensorimotor controller is achieved through an adaptation and reformulation of task-level control to address muscle-actuated biomechanical systems.

Sensorimotor control and biomechanical simulation provides several benefits. Human factors analysis is important in both product design and manufacturing process design. The controller offers transformative capabilities for the development of next generation human factors simulation that has the potential to reduce design cycle time and cost. For example, the controller can be implemented product design for performance enhancement, patient-focused rehabilitation technologies, and assistive robotic devices. Because each of these areas involve modeling, characterization, and simulation and prediction of human biomechanical performance, the controller provides significant impact by offering goal-oriented sensorimotor control to drive the needed biomechanical simulations. Specific details of the system (controller) are described in further detail below.

(3) Specific Details of the Invention

Figure 3:
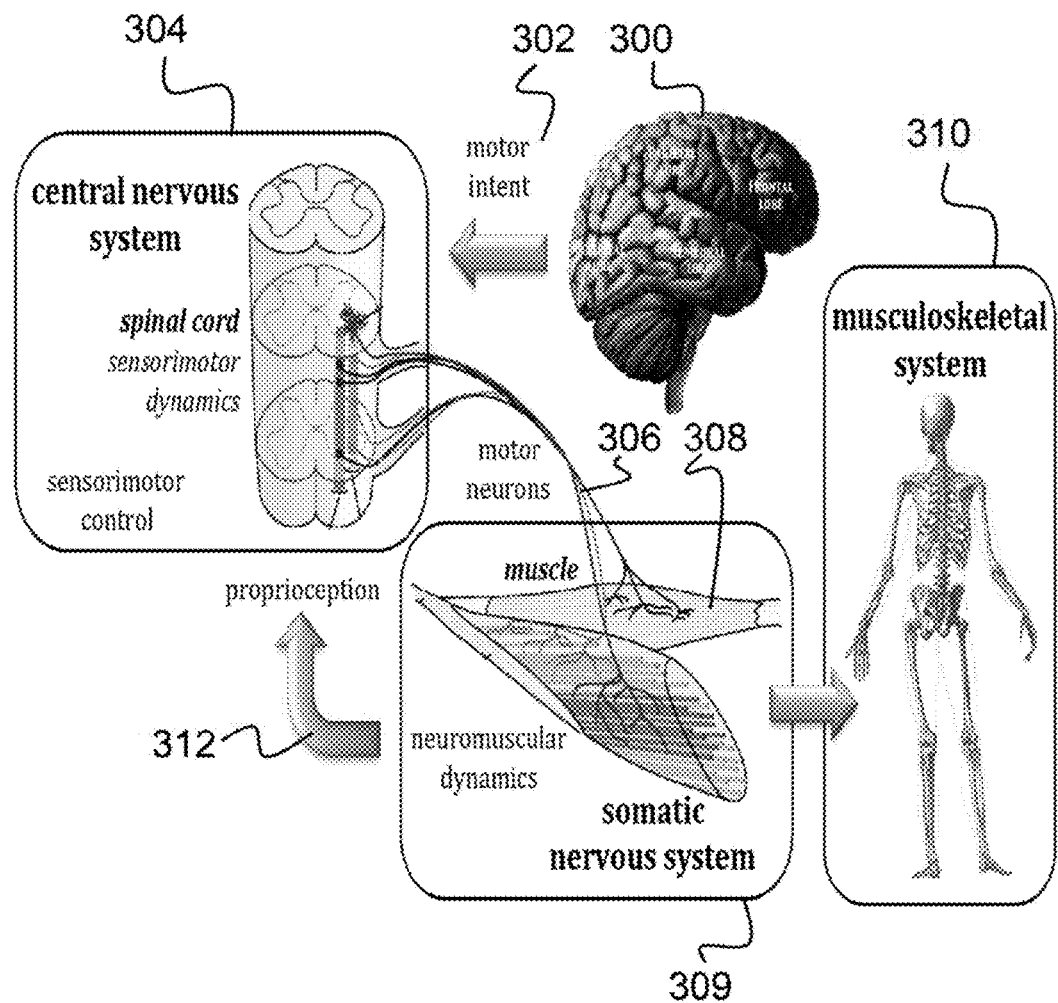
FIG. 3 is a flow chart illustrating the neural and musculoskeletal physiology associated with the motor control problem.

The system is designed to autonomously generate low-level neuromuscular control inputs to a musculoskeletal simulation based on high-level goal oriented commands. FIG. 3, for example, depicts the neural and musculoskeletal physiology associated with the motor control problem. High-level motor intent 300 from the brain 302 is transmitted to the central nervous system (CNS) 304. Sensorimotor integration and control results in the low-level command of motor neurons 306 innervating individual muscles 308 (in the somatic nervous system 309) to generate coordinated musculoskeletal 310 movement. Afferent proprioceptive signals 312 transmit sensory data from mechanoreceptors in the joints and tendons back to the CNS 304.

Figure 4:
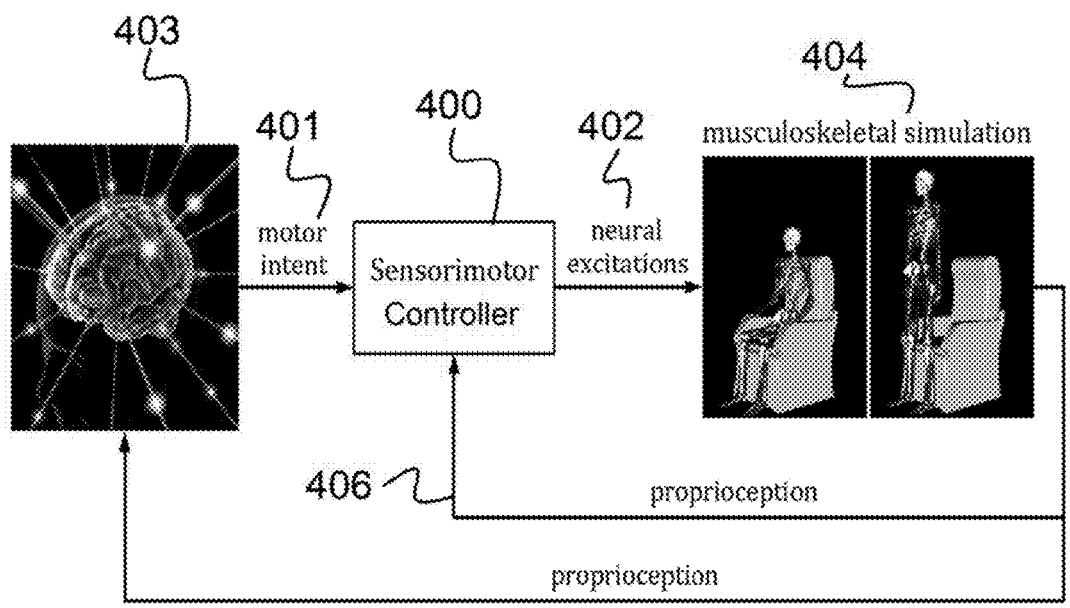
FIG. 4 is a functional block diagram depicting a system-level abstraction of FIG. 3, showing an abstracted representation of neural and musculoskeletal physiology.
Figure 7:
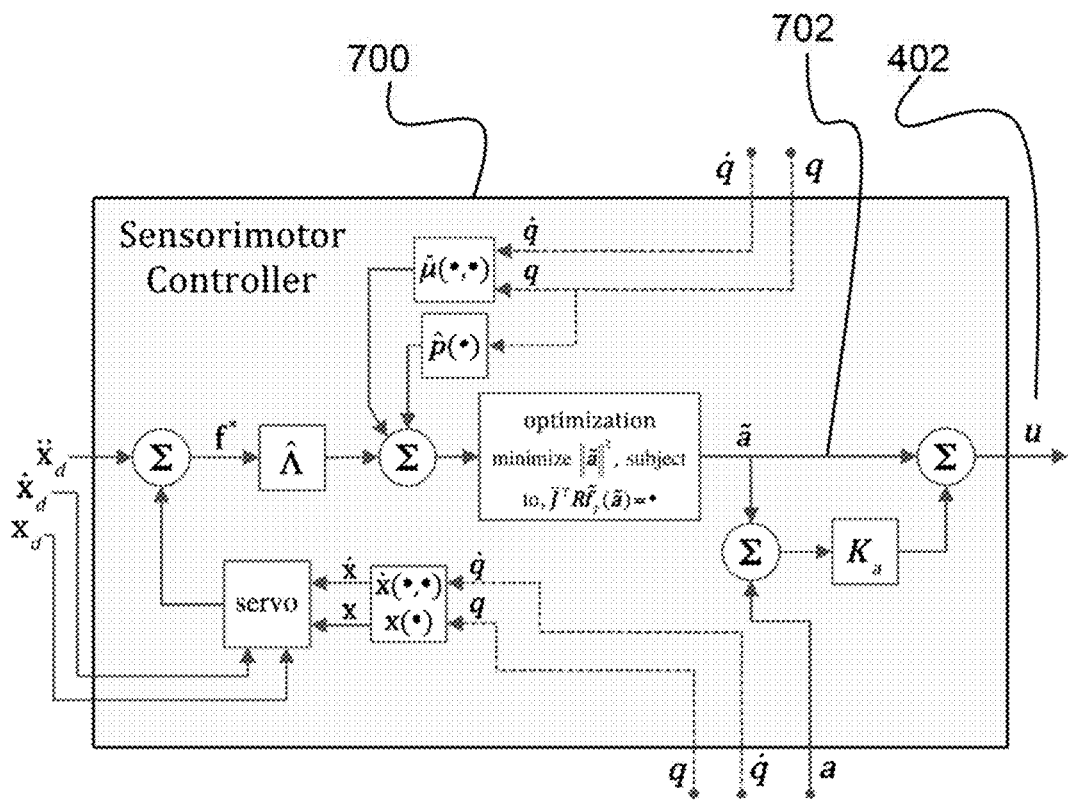
FIG. 7 is an illustration of a task-level sensorimotor controller according to the principles of the present invention.
Figure 10:
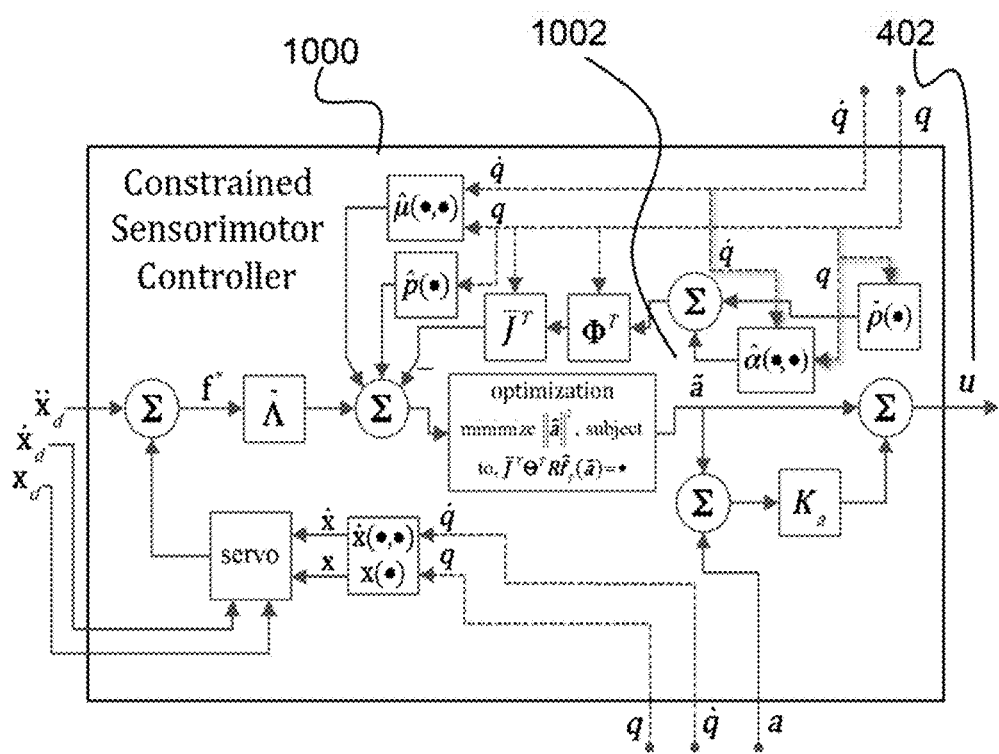
FIG. 10 is an illustration of a constrained task-level sensorimotor controller according to the principles of the present invention.
Figure 11:
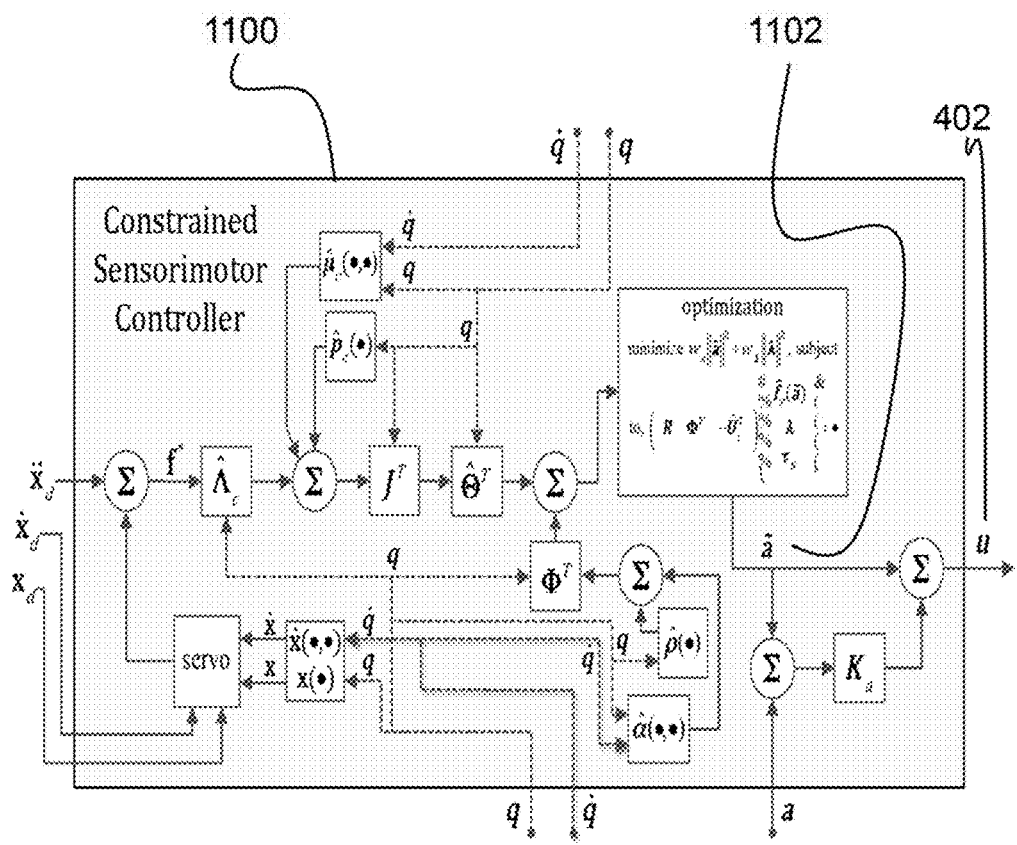
FIG. 11 is an illustration of a constrained task-level sensorimotor controller according to the principles of the present invention, which generates motion consistent with the input motion commands in the presence of holonomic system constraints.

FIG. 4 depicts a system-level abstraction of FIG. 3. The sensorimotor controller 400 is central to the controller described herein. It receives task-level command input (i.e., motor intent 401) from the human operator (or brain 403) and generates low-level neural excitations 402 for musculoskeletal simulations 404. This is a closed-loop control process where sensory data (via proprioceptive signals 406) is fed back to the sensorimotor controller 400, which provides continual updates to the neural excitations 402 driving the musculoskeletal simulation 404. Thus, in one aspect, the sensorimotor controller (simulator) operates by running musculoskeletal simulations on a musculoskeletal plant. The various aspects of the controller 400 are described in further detail below with respect to elements 700, 1000, and 1100 as illustrated in FIGS. 7, 10, and 11, respectively.

Figure 5:
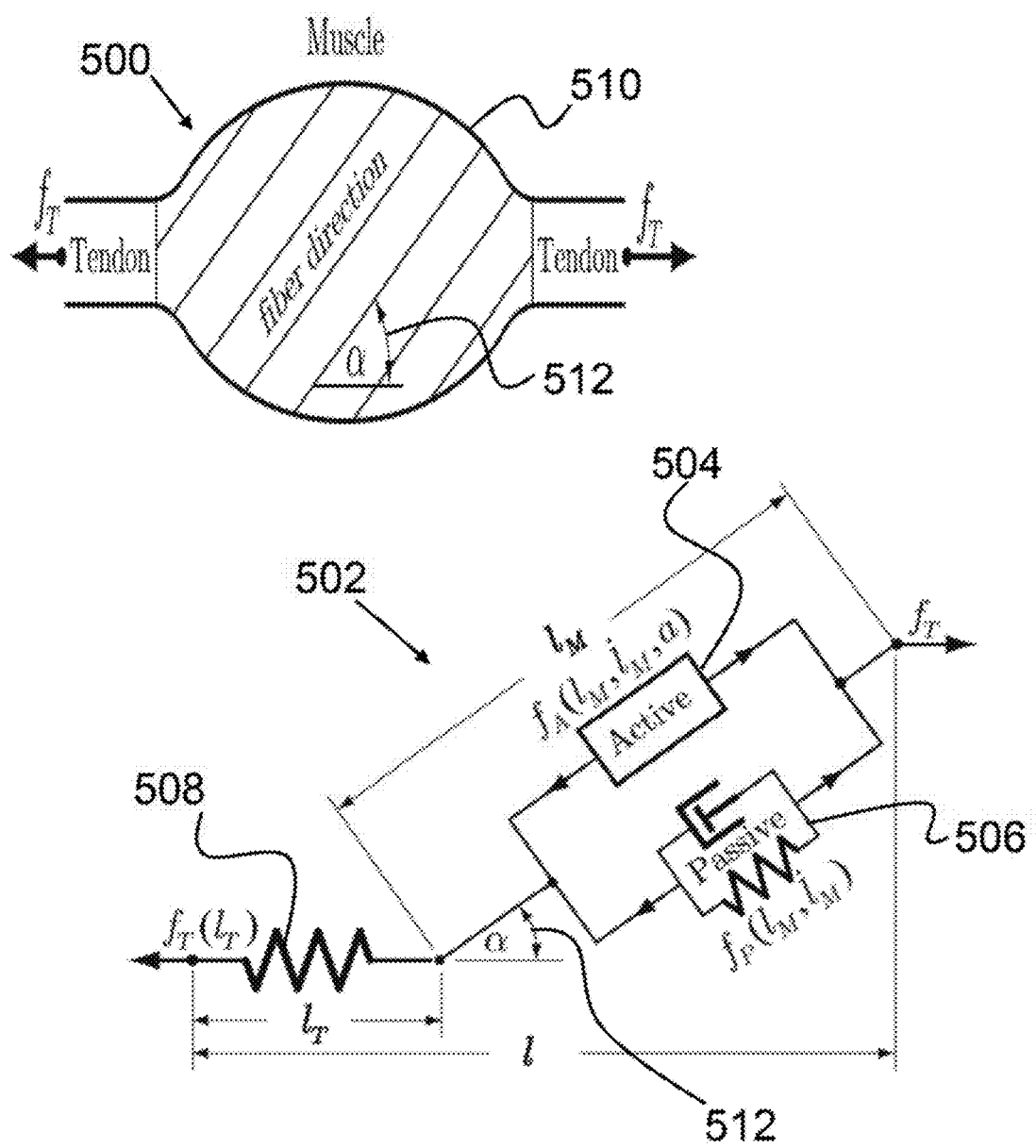
FIG. 5 is an illustration depicting an active state musculotendon model, where the active contractile element and passive viscoelastic element are in parallel and the passive elastic tendon element is in series.
Figure 6:
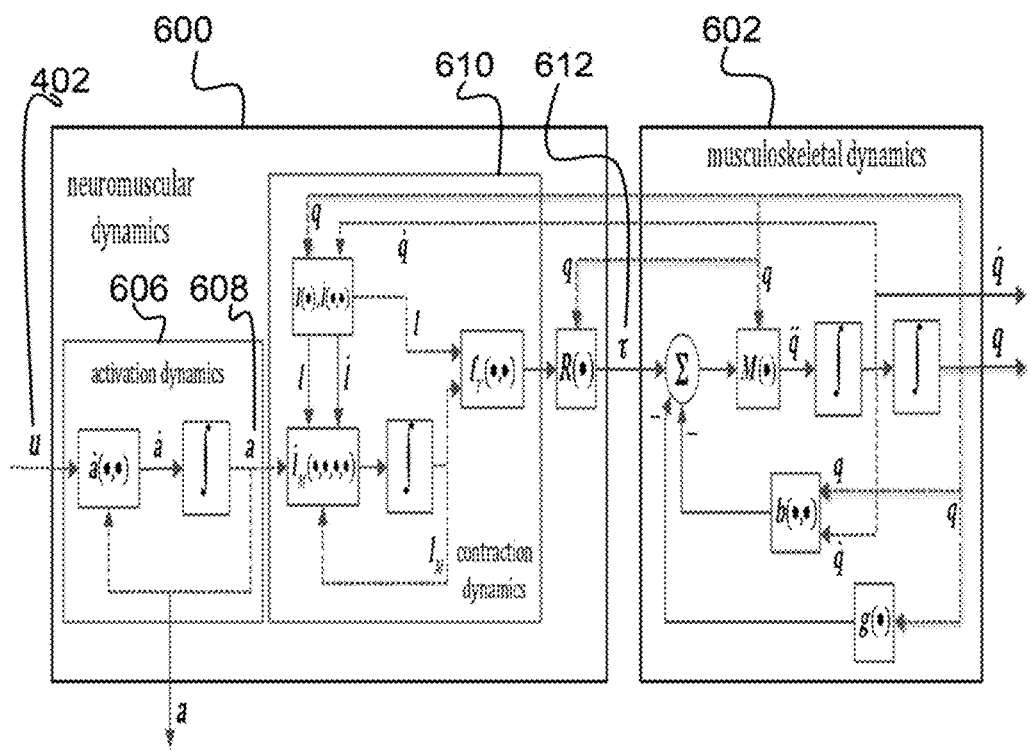
FIG. 6 is an illustration depicting a neuromuscular and musculoskeletal system (feed-forward path) according to the principles of the present invention.

For further understanding, FIG. 5 provides an illustration of an example musculoskeletal plant 500 according to the principles of the present invention. As shown in FIG. 6, the musculoskeletal plant (illustrated as element 404 in FIG. 4) can be divided in neuromuscular 600 dynamics and musculoskeletal 602 dynamics. Specifically, FIG. 6 is an illustration depicting a neuromuscular 600 and musculoskeletal 602 system (feed-forward path). As shown, neural excitations 402 provide input to the activation dynamics 606 and output 608 of the activation dynamics 606 provides input to the contraction dynamics 610. Further, output 612 of the contraction dynamics 610 provides input to the musculoskeletal 602 dynamics through the joint torques.

Further details regarding the neuromuscular 600 and musculoskeletal 602 systems are provided below. The musculoskeletal 602 system dynamics are described by the following system of equations in configuration space.

$$\tau = M(q)\ddot{q} + b(q,\dot{q}) + g(q),$$

where q is the vector of n generalized or joint coordinates, $\tau$, is the vector of applied joint torques, M(q), is the joint space mass matrix, $b(q,\dot{q})$, is the vector of centrifugal and Coriolis forces, and g(q) is the vector of gravity forces.

The neuromuscular 602 dynamics describe the behavior of a set of r musculotendon actuators spanning the musculoskeletal system. These actuators are modeled as Hill-type active state force generating units, as described by De Sapio, V., Khatib, O. and Delp, S. (2005) in 'Simulating the task-level control of human motion: a methodology and framework for implementation', The Visual Computer, Vol. 21, No. 5, pp. 289-302, which is hereby incorporated by reference as though fully set forth herein. It is assumed that the vector of r musculotendon lengths, l, can be uniquely determined from the system configuration, q. That is, l=l(q). As a consequence of this assumption, differential variations in l are given by, $$\delta l = \frac{\partial l}{\partial q}\delta q = L(q)\delta q,$$

where L(q) is the muscle Jacobian. From the principle of virtual work, it is concluded that, $$\tau = L^T f_T = R(q) f_T,$$

where $f_T$ is the vector of r tendon forces. The negative sign is due to the convention of taking contractile muscle forces as positive. The matrix of moment arms is denoted R.

The behavior of a set of r musculotendon actuators (neuromuscular dynamics 600) can be divided into activation dynamics 608 and contraction dynamics 610. Activation dynamics 608 refers to the process of muscle activation in response to neural excitation. This process can be modeled by the following equation of state written in terms of the vector of r muscle activations, $\alpha$, such that $$\dot{a} = \begin{pmatrix} \tau(u_1, a_1) & 0 & 0 \\ 0 & \ddots & 0 \\ 0 & 0 & \tau(u_r, a_r) \end{pmatrix}^{-1} (u-a),$$

where $a_i \in [0,1]$ and $u_i \in [0,1]$ is the neural input. The term $\tau(u_i, a_i)$ is a time constant given by, $$\tau(u_i, a_i) = \begin{cases} (\tau_a - \tau_d)u_i + \tau_d & \text{for } u_i \geq a_i \\ \tau_d & \text{for } u_1 < a_1 \end{cases},$$

where $\tau_a$ and $\tau_d$ are the activation and deactivation time constants, respectively.

The contraction dynamics of a single musculotendon unit (illustrated as element 500 in FIG. 5) can be modeled as the lumped parameter system 502. Referring again to FIG. 5, the lumped parameter system 502 describes the configuration of forces. There is an active element 504, a passive viscoelastic element (in parallel) 506, and an elastic tendon element (in series) 508. The relative angle associated with the muscle fibers 510, $\alpha$, is referred to as the pennation angle 512.

This yields the following relations, $$l(q) = l_M \cos \alpha + l_T,$$

$$\dot{l}(q) = \dot{l}_M \cos \alpha + \dot{l}_T,$$

where $l_M$ is the vector of muscle lengths and $l_T$ is the vector of tendon lengths. The following force equilibrium equations can be expressed, $$f_T = (f_A + f_P) \cos \alpha,$$

where $f_A$ is the vector of active forces in the muscles and $f_p$ is the vector of passive forces in the muscles. Using this force equilibrium equation as well as constitutive relationships describing muscle forces as a function of muscle length and contraction velocity, $f_A(l_M, \dot{l}_M, \alpha)$ and $f_p(l_M, \dot{l}_M)$, and tendon force as a function of tendon length, $f_T(l_T)$, the following equation of state in functional form can be expressed as, $$\dot{l}_M = \dot{l}_M(l(q), \dot{l}(q,\dot{q}), l_M, \alpha).$$

So, for a system of r musculotendon actuators, the following system of 2r first-order state equations can be expressed as, $$\dot{a} = \dot{a}(u,a) = \begin{pmatrix} \tau(u_1, a_1) & 0 & 0 \\ 0 & \ddots & 0 \\ 0 & 0 & \tau(u_r, a_r) \end{pmatrix}^{-1} (u-a),$$

and, $\dot{l}_M = \dot{l}_M(l(q), \dot{l}(q,\dot{q}), l_M, a)$, where the internal states are $l_M$ and $\alpha$. This is complemented by the force relationship, $$f_T = f_T(l_T) = l(q) - l_M \cos \alpha = f_T(l(q), l_M).$$

Returning to the musculoskeletal dynamics (depicted as element 602 in FIG. 6), $$\tau = M(q)\ddot{q} + b(q,\dot{q}) + g(q),$$

these equations of motion can be mapped into operational or task space, as follows:

$$J^T\tau = J^T[M(q)\ddot{q}+b(q,\dot{q})+g(q)] \rightarrow$$
$$J^T\tau = f = \Lambda(q)\ddot{x}+p(q,\dot{q})+p(q),$$

where $\bar{J}$ is the dynamically consistent inverse of the task Jacobian, x is a description of task coordinates that are to be controlled, f, are the control forces that act at the task, and $\Lambda(q)$, $\mu(q, \dot{q})$, and $p(q)$, are the task space mass matrix, centrifugal and Coriolis force vector, and gravity force vector, respectively. See Khatib, O. (1995) in 'Inertial properties in robotic manipulation: an object level framework', International Journal of Robotics Research, Vol. 14, No. 1. pp. 19-36, for a discussion of task space, which is hereby incorporated by reference as through fully set forth herein.

Given a system of r musculotendon actuators, the applied joint torques are given by, $$\tau = Rf_T,$$

which provides the following muscle actuated task space equations of motion, $$J^T Rf_T = \Lambda \ddot{x} + \mu + p.$$

For control purposes, the muscle actuated task space equations of motion can be expressed as:

$$J^T Rf_T = \hat{\Lambda} f^* + \hat{\mu} + \hat{p}.$$

where $\hat{\cdot}$ represents estimates of the dynamic parameters and $f^*$ is the control law. Since the term $J^T Rf_T$ is underdetermined it offers many solutions for $f_T$. These solutions correspond to the kinematic redundancy associated with the task and the actuator redundancy associated with the system of musculotendon force actuators. In the computed muscle control approach of Thelen et al., (2003), Thelen and Anderson, (2006) there was only muscle redundancy that needed to be resolved. This was achieved through a static optimization step. In the task-level formulation as used herein, a static optimization, computed each time step in the simulation, is also specified to resolve both muscle redundancy and kinematic redundancy. Specifically, a set of muscle activations, ã, is determined, which minimizes $\|\tilde{a}\|^2$, where ã are muscle activations associated with the steady state tendon forces $\hat{f}_T(\tilde{a})$ (i.e., tendon forces at a time when the contraction dynamics have equilibrated and the transients have decayed). Further these activations must generate steady state tendon forces that satisfy the task motion requirements, $$J^T R\hat{f}_T(\tilde{a}) = \hat{\Lambda} f^* + \hat{\mu} + \hat{p}.$$

Using a linear proportional controller, a set of neural excitations, u, is computed which causes the actual activations, a, from the forward neuromuscular simulation to track ã, as follows:

$$u = \tilde{a} + K_a(\tilde{a} - a),$$

where $K_a$ is the gain. This task-level input computed muscle control architecture is depicted in FIG. 7. FIG. 7 is an illustration of a task-level sensorimotor controller 700 according to the principles of the present invention, where motion commands are represented in task space. The controller 700 generates optimal neural excitation 402 commands that minimize muscle activation 702, and generate motion consistent with the input motion commands.

Figure 8:
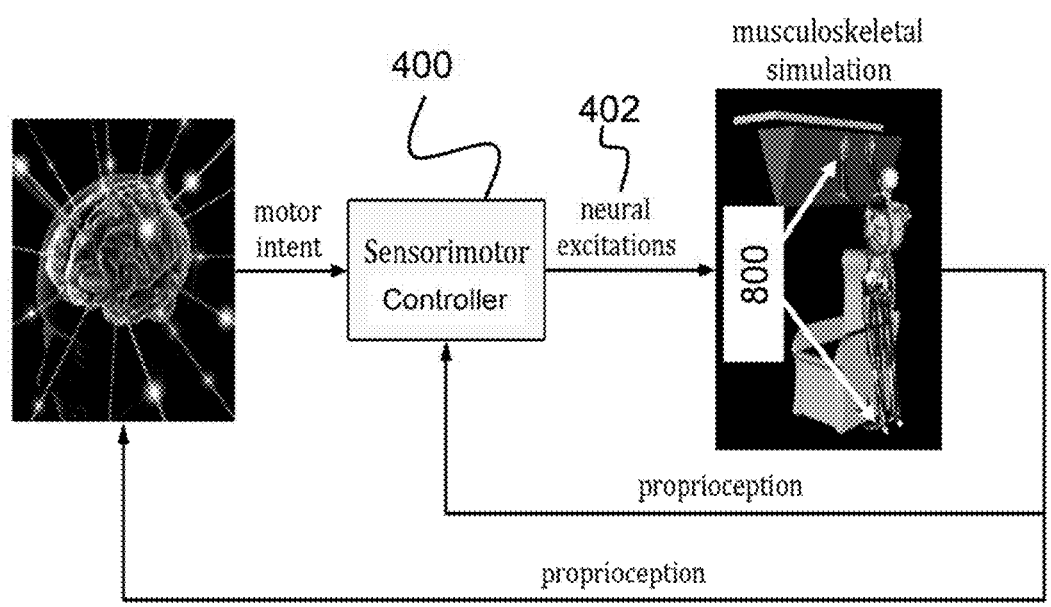
FIG. 8 is a functional block diagram depicting an abstracted representation of neural and musculoskeletal physiology.

Further and as shown in FIG. 8, holonomic constraints 800 can be incorporated into the system. Specifically, FIG. 8 illustrates a functional block diagram showing an abstracted representation of neural and musculoskeletal physiology. In one aspect, the sensorimotor controller 400 is a goal-oriented neuromuscular feedback controller that drives the constrained 800 musculoskeletal simulation by specifying low-level neural 402 excitations that execute task-level commands. Specific examples of constrained versions of the sensorimotor controller 400 are depicted in FIGS. 10 and 11 as elements 1000 and 1100, respectively.

Figure 9:
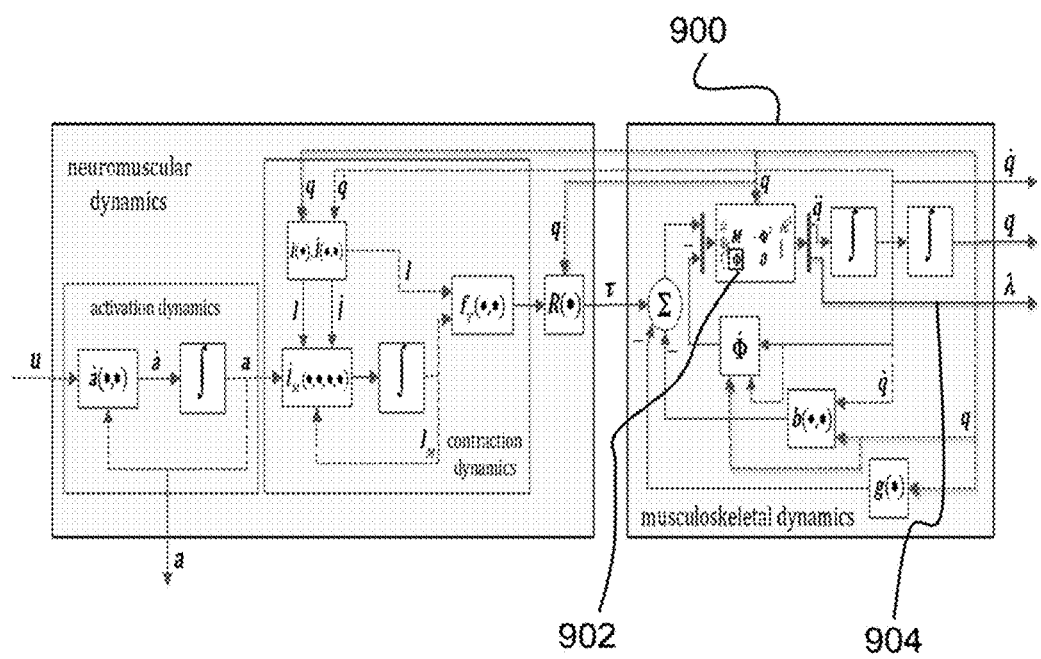
FIG. 9 is an illustration depicting a neuromuscular and musculoskeletal system (feed-forward path), showing the musculoskeletal system dynamics augmented with a set of holonomic constraints and Lagrange multipliers.

Further and as shown in FIG. 9, the holonomic constraints, $\phi(q)=0$, can be incorporated into the musculoskeletal dynamics. The configuration space dynamics was augmented with Lagrange multipliers, $\lambda$, $$\tau = M(q)\ddot{q} + b(q,\dot{q}) + g(q) - \Phi^T\lambda,$$

where $\Phi^T$ is the constraint Jacobian. The block diagram of the constrained musculoskeletal system is depicted in FIG. 9. Specifically, FIG. 9 is an illustration depicting a neuromuscular and constrained musculoskeletal system (feedforward path), showing the musculoskeletal system dynamics 900 augmented with a set of holonomic constraints 902 and Lagrange multipliers 904.

The approach expresses these dynamics in one of two ways. First, as shown in FIG. 10, the constrained dynamics can be represented in task space as:

$$\bar{J}^T \Theta^T {}^T\tau = \Lambda(q)\ddot{x} + \mu(q,\dot{q}) + p(q) - \bar{J}^T \Phi^T(\alpha + \rho),$$

where $\Theta^T$ is the constraint null space projection matrix. Task space representations were described by De Sapio, V., Khatib, O., and Delp, S. (2006), in 'Task-level approaches for the control of constrained multibody systems', Multibody System Dynamics, Vol. 16, No. 1, pp. 73-102, which is hereby incorporated by reference as through fully set forth herein. The centrifugal and Coriolis forces, and gravity forces projected at the constraints are $\alpha$ and $\rho$ respectively. For neuromuscular control purposes, this can be expressed as the following muscle actuated task space equations of motion, $$\bar{J}^T \Theta^T Rf_T = \hat{\Lambda} f^* + \hat{\mu} + \hat{p} - \bar{J}^T \Phi^T(\hat{\alpha} + \hat{\rho}).$$

As before, the controller 1000 seeks ã 1002, which minimizes $\|\tilde{a}\|^2$ (i.e., magnitude squared of the activations) to generate the neural excitations 402. Further these activations 1002 must generate steady state tendon forces that satisfy the constrained task motion requirements, as follows:

$$\bar{J}^T \Theta^T R\hat{f}_T = \hat{\Lambda} f^* + \hat{\mu} + \hat{p} - \bar{J}^T \Phi^T(\hat{\alpha} + \hat{\rho}).$$

Alternately and as shown in FIG. 11, constrained dynamics can be represented in task space as $$\tau = \Theta^T {}^T J^T(\Lambda_c \ddot{x} + \mu_c + p_c) + \Phi^T(\alpha + \rho) + U_c^T \tau_N - \Phi^T \lambda,$$

where $\Theta^T {}^T$ is the constraint null space projection matrix, $\Lambda_c$, $\mu_c$, $p_c$, are the task/constraint space mass matrix, centrifugal and Coriolis force vector, and gravity force vector, respectively. Task space representations were further described by De Sapio, V. (2011), in 'Task-level control of motion and constraint forces in holonomically constrained robotic systems', in Proceedings of the 18th World Congress of the International Federation of Automatic Control, and De Sapio, V. and Park, J. (2010), in 'Multitask constrained motion control using a mass-weighted orthogonal decomposition', Journal of Applied Mechanics, Vol. 77, No. 4, p. 041004, both of which are hereby incorporated by reference as though fully set forth herein. The centrifugal and Coriolis forces, and gravity forces projected at the constraints are $\alpha$ and $\rho$ respectively. Finally, $U_c^T$ is the combined null space projection matrix, with respect to both task and constraints, and $\tau_N$ is the control vector for the null space.

This representation exposes the constraint forces and is useful for generating optimal neural excitations that track task motion under constraints and also minimizes specific internal joint reaction forces. For neuromuscular control purposes, this can be expressed as the following muscle actuated task space equations of motion, $$R\tilde{f}_T + \Phi^T \lambda - \tilde{U}_c^T \tau_N = \Phi^T J^T (\tilde{\Lambda}_c f^* + \hat{\mu}_c + \hat{p}_c) + \Phi^T (\hat{\alpha} + \hat{p}).$$

Thus, the system now seeks ã and λ, which minimize $w_a\|\tilde{a}\|^2 + w_\lambda\|\lambda\|^2$. Further these activations must generate steady state tendon forces that satisfy the constrained task motion requirements, $$(R \quad \Phi^T \quad -\hat{U}_c^T)\begin{pmatrix}\tilde{f}_T(\tilde{a}) \\ \lambda \\ \tau_N\end{pmatrix} = \Theta^T J^T(\tilde{\Lambda}_c f^* + \hat{\mu}_c + \hat{p}_c) + \Phi^T(\hat{\alpha} + \hat{p}).$$

Thus, FIG. 11 is an illustration of a constrained task-level sensorimotor controller 1100 based on a reformulation of the computed muscle control approach. The system represents motion commands in task space and generates optimal neural excitation 402 commands that minimize muscle activation 1102, and generates motion consistent with the input motion commands in the presence of holonomic system constraints.

What is claimed is:

1. A goal-oriented sensorimotor controller for generating musculoskeletal simulations with excitation commands, comprising:
   one or more sensors for acquiring neural sensory data from a human operator;
   one or more processors and a memory, the memory having executable instructions encoded thereon, such that upon execution of the instructions, the one or more processors perform operations of:
   receiving a task-level motion command for motion of a musculoskeletal system from the human operator, the musculoskeletal system having holonomically constrained musculoskeletal dynamics that include steady state tendon forces;
   generating, based on the task-level motion command, a set of required muscle activations that minimizes a magnitude squared of the set of required muscle activations amongst a set of all possible muscle activations, where the set of the required muscle activations are associated with the steady state tendon forces;
   generating a set of excitation commands that is consistent with the minimization of the magnitude of required muscle activations amongst the set of all possible muscle activations to generate motion consistent with the task-level motion command; and
   acquiring neural sensory data from the human operator and updating the set of excitation commands based on the neural sensory data.

2. The goal-oriented sensorimotor controller as set forth in claim 1, wherein the musculoskeletal dynamics of the musculoskeletal system is augmented with holonomically constrained system dynamics and Lagrange multipliers.

3. The goal-oriented sensorimotor controller as set forth in claim 2, wherein the set of excitation commands, u, is computed which causes the actual activations, a, from the forward neuromuscular simulation to track ã, using a linear proportional controller $u=\tilde{a}+K_a(\tilde{a}-a)$, where $K_a$ is the gain.

4. The goal-oriented sensorimotor controller as set forth in claim 3, wherein the holonomically constrained musculoskeletal system dynamics are represented in task space as:

$$(R \quad \Phi^T \quad -\hat{U}_c^T)\begin{pmatrix}\tilde{f}_T(\tilde{a}) \\ \lambda \\ \tau_N\end{pmatrix} = \Theta^T J^T(\tilde{\Lambda}_c f^* + \hat{\mu}_c + \hat{p}_c) + \Phi^T(\hat{\alpha} + \hat{p})$$

where $\widehat{\cdot}$ represents estimates of the dynamic parameters, $\Theta^T$ is a constraint null space projection matrix, where $J^T$ is a task Jacobian (transposed), $\Phi^T$ is a constraint Jacobian, R is a matrix of muscle moment arms, ã are muscle activations associated with the steady state tendon forces $\tilde{f}_T(\tilde{a})$ (i.e., tendon forces at a time when the contraction dynamics have equilibrated and the transients have decayed), where $\Lambda_c$, $\mu_c$, $p_c$, are the task/constraint space mass matrix, centrifugal and Coriolis force vector, and gravity force vector, respectively, and where the centrifugal and Coriolis forces, and gravity forces projected at the constraints are α and ρ respectively, where $U_c^T$ is the combined null space projection matrix, with respect to both task and constraints, and where $\tau_N$ is the control vector for the null space, and where λ is a Lagrange multipliers, and where f* is the control law.

5. The goal-oriented sensorimotor controller as set forth in claim 1, wherein the set of excitation commands, u, is computed which causes the actual activations, a, from the forward neuromuscular simulation to track ã, using a linear proportional controller $u=\tilde{a}+K_a(\tilde{a}-a)$, where $K_a$ is the gain.

6. A goal-oriented method for generating musculoskeletal simulations with excitation commands, comprising an act of:
   executing, with one more processors, executable instructions encoded on a memory, such that upon execution of the instructions, the one or more processors perform operations of:
   receiving, in the one or more processors, a task-level motion command from a human operator for motion of a musculoskeletal system, the musculoskeletal system having holonomically constrained musculoskeletal dynamics that include steady state tendon forces;
   generating, based on the task-level motion command, a set of required muscle activations that minimizes a magnitude squared of the set of required muscle activations amongst a set of all possible muscle activations, where the set of the required muscle activations are associated with the steady state tendon forces;
   generating a set of excitation commands that is consistent with the minimization of the magnitude of required muscle activations amongst the set of all possible muscle activations to generate motion consistent with the task-level motion command; and
   acquiring neural sensory data from the human operator and updating the set of excitation commands based on the neural sensory data.

7. The goal-oriented method as set forth in claim 6, wherein the musculoskeletal dynamics of the musculoskeletal system is augmented with holonomically constrained system dynamics and Lagrange multipliers.

8. The goal-oriented method as set forth in claim 7, wherein the set of excitation commands, u, is computed which causes the actual activations, a, from the forward neuromuscular simulation to track ã, using a linear proportional controller $u=\tilde{a}+K_a(\tilde{a}-a)$, where $K_a$ is the gain.

9. The goal-oriented method as set forth in claim 8, wherein the holonomically constrained musculoskeletal system dynamics are represented in task space as:

$$(R \quad \Phi^T \quad -\hat{U}_c^T) \begin{pmatrix} \hat{f}_T(\tilde{a}) \\ \lambda \\ \tau_N \end{pmatrix} = \Theta^T J^T (\tilde{\Lambda}_c f^* + \hat{\mu}_c + \hat{p}_c) + \Phi^T (\hat{\alpha} + \hat{p})$$

where $\widehat{\cdot}$ represents estimates of the dynamic parameters, $\Phi^T$ is a constraint null space projection matrix, where $J^T$ is a task Jacobian (transposed), $\Phi^T$ is a constraint Jacobian, R is a matrix of muscle moment arms, ã are muscle activations associated with the steady state tendon forces $\tilde{f}_T(\tilde{a})$ (i.e., tendon forces at a time when the contraction dynamics have equilibrated and the transients have decayed), where $\Lambda_c$, $\mu_c$, $p_c$, are the task/constraint space mass matrix, centrifugal and Coriolis force vector, and gravity force vector, respectively, and where the centrifugal and Coriolis forces, and gravity forces projected at the constraints are $\alpha$ and $\rho$ respectively, where $U_c^T$ is the combined null space projection matrix, with respect to both task and constraints, and where $\tau_N$ is the control vector for the null space, and where $\lambda$ is a Lagrange multipliers, and where f* is the control law.

10. The goal-oriented sensorimotor controller as set forth in claim 6, wherein the set of excitation commands, u, is computed which causes the actual activations, a, from the forward neuromuscular simulation to track ã, using a linear proportional controller u=ã+$K_a$(ã-a), where $K_a$ is the gain.

11. A computer program product for generating musculoskeletal simulations with excitation commands, the computer program product comprising:
a non-transitory computer-readable medium having executable instructions encoded thereon, such that upon execution of the instructions by one or more processors, the one or more processors perform operations of:
receiving a task-level motion command from a human operator for motion of a musculoskeletal system, the musculoskeletal system having holonomically constrained musculoskeletal dynamics that include steady state tendon forces;
generating, based on the task-level motion command, a set of required muscle activations that minimizes a magnitude squared of the set of required muscle activations amongst a set of all possible muscle activations, where the set of the required muscle activations are associated with the steady state tendon forces;
generating a set of excitation commands that is consistent with the minimization of the magnitude of required muscle activations amongst the set of all possible muscle activations to generate motion consistent with the task-level motion command; and
acquiring neural sensory data from the human operator and updating the set of excitation commands based on the neural sensory data.

12. The computer program product as set forth in claim 11, wherein the musculoskeletal dynamics of the musculoskeletal system is augmented with holonomically constrained system dynamics and Lagrange multipliers.

13. The computer program product as set forth in claim 12, wherein the set of excitation commands, u, is computed which causes the actual activations, a, from the forward neuromuscular simulation to track ã, using a linear proportional controller u=ã+$K_a$(ã-a), where $K_a$ is the gain.

14. The computer program product as set forth in claim 13, wherein the holonomically constrained musculoskeletal system dynamics are represented in task space as:

$$(R \quad \Phi^T \quad -\hat{U}_c^T) \begin{pmatrix} \hat{f}_T(\tilde{a}) \\ \lambda \\ \tau_N \end{pmatrix} = \Theta^T J^T (\tilde{\Lambda}_c f^* + \hat{\mu}_c + \hat{p}_c) + \Phi^T (\hat{\alpha} + \hat{p})$$

where $\widehat{\cdot}$ represents estimates of the dynamic parameters, $\Theta^{T\,T}$ is a constraint null space projection matrix, where $J^T$ is a task Jacobian (transposed), $\Phi^T$ is a constraint Jacobian, R is a matrix of muscle moment arms, ã are muscle activations associated with the steady state tendon forces $\tilde{f}_T(\tilde{a})$ (i.e., tendon forces at a time when the contraction dynamics have equilibrated and the transients have decayed), where $\Lambda_c$, $\mu_c$, $p_c$, are the task/constraint space mass matrix, centrifugal and Coriolis force vector, and gravity force vector, respectively, and where the centrifugal and Coriolis forces, and gravity forces projected at the constraints are $\alpha$ and $\rho$ respectively, where $U_c^T$ is the combined null space projection matrix, with respect to both task and constraints, and where $\tau_N$ is the control vector for the null space, and where $\lambda$ is a Lagrange multipliers, and where f* is the control law.

15. The computer program product as set forth in claim 11, wherein the set of excitation commands, u, is computed which causes the actual activations, a, from the forward neuromuscular simulation to track ã, using a linear proportional controller u=ã+$K_a$(ã-a), where $K_a$ is the gain.

* * * * *